(12) United States Patent
Despa et al.

(10) Patent No.: US 11,628,258 B2
(45) Date of Patent: Apr. 18, 2023

(54) CONTROLLED DELIVERY SYRINGE DEVICE

(71) Applicant: Becton, Dickinson and Company, Franklin Lakes, NJ (US)

(72) Inventors: Mircea Despa, Cary, NC (US); Matthew Ferriter, Chapel Hill, NC (US); Adam Martin, Morrisville, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 750 days.

(21) Appl. No.: 16/604,396

(22) PCT Filed: Apr. 5, 2018

(86) PCT No.: PCT/US2018/026222
§ 371 (c)(1),
(2) Date: Oct. 10, 2019

(87) PCT Pub. No.: WO2018/191101
PCT Pub. Date: Oct. 18, 2018

(65) Prior Publication Data
US 2020/0121857 A1     Apr. 23, 2020

Related U.S. Application Data
(60) Provisional application No. 62/485,056, filed on Apr. 13, 2017.

(51) Int. Cl.
*A61M 5/00*     (2006.01)
*A61M 5/315*    (2006.01)

(52) U.S. Cl.
CPC .... *A61M 5/31501* (2013.01); *A61M 5/31511* (2013.01); *A61M 5/31568* (2013.01);
(Continued)

(58) Field of Classification Search
CPC .............. A61M 5/315; A61M 5/31501; A61M 5/31505; A61M 2005/31508;
(Continued)

(56) References Cited

U.S. PATENT DOCUMENTS 4,466,426 A     8/1984  Blackman
4,642,102 A *   2/1987  Ohmori ............... A61M 5/3158
                                                        604/220
(Continued)

FOREIGN PATENT DOCUMENTS

EP      3072547 A1     9/2016
WO   2018009357 A1     1/2018

*Primary Examiner* — Rebecca E Eisenberg
(74) *Attorney, Agent, or Firm* — The Webb Law Firm (57) ABSTRACT

A controlled delivery syringe device includes a syringe barrel having a proximal end and distal end which defines a chamber for containing an injectable material. A plunger rod is associated with the syringe barrel and a plunger is secured thereto which is axially movable within the syringe barrel. A plurality of equally and sequentially spaced periodic features are associated with the plunger rod and a counter member is engageable with the periodic features. Application of a distally directed force to the plunger rod results in disengagement and reengagement of the counter member with the sequentially spaced periodic features on the plunger rod, enabling advancement of the plunger rod and plunger in the syringe barrel while providing tactile feedback of dose progression of the injectable material. A method of retrofitting a syringe with a device for injecting a metered dose of injectable material is also provided.

12 Claims, 9 Drawing Sheets

(52) U.S. Cl.
CPC ............... *A61M 5/31595* (2013.01); *A61M 2005/31508* (2013.01); *A61M 2207/00* (2013.01)

(58) Field of Classification Search
CPC ........... A61M 2005/3151; A61M 2005/31506; A61M 5/31511; A61M 5/31568; A61M 5/31595
See application file for complete search history.

(56) References Cited

U.S. PATENT DOCUMENTS

| | | |
|---|---|---|
| 4,915,695 A | 4/1990 | Koobs |
| 8,939,959 B2 | 1/2015 | Baney et al. |
| 2013/0197449 A1 | 8/2013 | Franklin |
| 2014/0031763 A1 | 1/2014 | Soma et al. |
| 2014/0276588 A1 | 9/2014 | Li et al. |
| 2015/0359969 A1* | 12/2015 | Armstrong .......... A61M 5/3134 604/221 |
| 2016/0144122 A1 | 5/2016 | Locati et al. |
| 2018/0001032 A1 | 1/2018 | Kleyman et al. |
| 2018/0085529 A1 | 3/2018 | Törnsten et al. |

* cited by examiner

CONTROLLED DELIVERY SYRINGE DEVICE

CROSS-REFERENCE TO RELATED APPLICATIONS

This application is the United States national phase of International Application No. PCT/US2018/02622 filed Apr. 5, 2018, and claims priority to U.S. Provisional Application Ser. No. 62/485,056 entitled "Controlled Delivery Syringe Device" filed Apr. 13, 2017, the disclosures of which are hereby incorporated by reference in their entirety.

BACKGROUND OF THE INVENTION

Field of the Invention

The invention relates, in general, to a syringe for the controlled delivery of a metered dose of injectable product, and, more particularly, to a syringe including features to assist in the delivery of medications when direct observation of the syringe barrel is difficult, and even more particularly, to a syringe that includes a tactile feedback of dose progression and additional features that prevent catastrophic backflow caused by line pressure during use with medical devices.

Description of Related Art

Dose dividing delivery devices are known for dividing injectable material into multiple sub-doses for injection through a needle, such as for the delivery of drugs, vaccines, and the like. One such example is disclosed in U.S. Pat. No. 8,939,959. This dose dividing delivery device uses a ratcheting mechanism built into the plunger rod to enable multi-site injections. The device disclosed in the patent requires the medical practitioner to use two hands to operate the device as it includes the steps of stopping at each interval and actuating in a radial direction to enable administration of the next increment or dose.

Certain medical devices are used for treatment of individuals that require the administration of a metered dose of injectable material. One such medical device is a dialysis machine. During a hemodialysis treatment, iron is administered to a patient to compensate for losses associated with blood filtration. The normal administration practice for iron medication comprises delivering the doses with several pushes of a syringe device while the dialysis treatment is undergoing. During the process, medical practitioners are required to inject the medication into an external blood loop of the hemodialysis machine. Often, the orientation of the syringe and ergonomics of the operation are such that direct observation of the movement of the stopper inside the syringe barrel is hindered. This makes it difficult for the practitioner to regulate or monitor the amount of the fluid being injected. Oftentimes, the practitioner has to estimate the amount of fluid being injected based on the movement of the plunger within the syringe.

In addition, the injection is done in the external blood loop, which is under elevated pumping pressure from the dialysis machine. Consequently, if the syringe is left unattended while connected to the loop, the stopper can be pushed back out of the barrel by the pressure in the loop. This can result in blood being expelled out at a high rate. To prevent this, currently, at the end of each push, the medical practitioner clamps the "pigtail" tubing line, connecting the syringe to the blood loop, to isolate the syringe from the blood loop pressure. Since the iron is administered in multiple periodic pushes, there are several times when the clamp is actuated on the line. This requires a significant amount of care by the practitioner to prevent a catastrophic blow-back event.

Accordingly, there is a need in the art for a syringe fitted with a mechanism that provides a tactile feedback to the practitioner informing of dose progression. There is further a need in the art for the practitioner to monitor the volume of the fluid that is injected. There is also a need for a device that automatically locks and prevents the stopper from being pushed back and out of the syringe. This type of device would provide an added layer of protection against a catastrophic failure resulting from clamp failure. Additionally, it would be desirable to provide a syringe that can be operated single-handed, which would free up the practitioner's other hand to perform additional functions.

SUMMARY OF THE INVENTION

In accordance with an embodiment of the present invention, a controlled delivery syringe device includes a syringe barrel having a proximal end and distal end which defines a chamber therein. The chamber is configured for containing an injectable material. A plunger rod is associated with the syringe barrel and a plunger is secured to the plunger rod and axially movable within the syringe barrel. A plurality of equally and sequentially spaced periodic features are associated with at least a portion of the plunger rod and a counter member is engageable with the periodic features. The plunger rod is configured so that the application of a distally directed force thereto results in disengagement and reengagement of the counter member with the sequentially spaced periodic features on the plunger rod, enabling advancement of the plunger rod and plunger in the syringe barrel while providing tactile feedback of dose progression of the injectable material. Reengagement of the counter member with the sequentially spaced periodic features prevents retraction of the plunger rod and plunger within the syringe barrel.

According to one embodiment, the plunger rod comprises a thumb press located at a proximal end of the plunger rod to receive the application of the distally directed force to the plunger rod resulting in disengagement and reengagement of the counter member with the sequentially spaced periodic feature on the plunger rod. The periodic features can be angled such that upon disengagement of the counter member therefrom, the angled surface of the features can apply an outwardly directed force to the counter member, pushing the counter member out of the way so that the plunger rod can advance.

The device can also include an actuating member comprising at least one tab having an engagement end and a finger press end and wherein application of a pivoting force to the at least one tab results in disengagement and reengagement of the counter member with a sequentially spaced periodic feature on the plunger rod enabling retraction of the plunger rod and plunger within the syringe barrel. It can be appreciated that actuation of the actuation member would also enable the practitioner to advance the plunger rod within the syringe barrel. The counter member can comprise the engagement end of the at least one tab and the engagement end engages the periodic features.

According to one design, the periodic features can be provided on oppositely disposed sides of the plunger rod. In this design, the counter member can comprise a pair of oppositely disposed tabs, each of the tabs including an engagement end and a finger press end and wherein the engagement ends engages the periodic features. The oppositely disposed tabs can be configured to pivot upon the application of a squeezing force to the finger press ends of the tabs, causing the engagement end of the tabs to disengage from the periodic features, enabling retraction or advancement of the plunger rod and plunger in the syringe barrel.

The counter member can include a collar configured for clamping about a distal end of the syringe barrel. According to one design, the collar of the counter member comprises a plurality of separable components capable of being permanently secured about a flange of the syringe barrel, such that the collar of the counter member overhangs a rear opening of the syringe barrel.

In accordance with another embodiment of the present invention, a method of retrofitting a syringe with a device for injecting a metered dose of injectable material includes the steps of providing a syringe barrel having a proximal end and distal end defining a chamber therein, the chamber configured for containing an injectable material, providing a plunger rod having a proximal end and a distal end and a plunger secured to the distal end thereof, the plunger rod further including a plurality of equally and sequentially spaced periodic features located thereon, associating the plunger rod and plunger with the syringe barrel such that the plunger is axially movable within the syringe barrel, and securing a counter member onto a distal end of the syringe barrel, the counter member including at least one tab associated with the periodic features on the plunger rod. Application of a distally directed force to the plunger rod results in disengagement and reengagement of the counter member with a sequentially spaced periodic feature on the plunger rod, enabling advancement of the plunger rod and plunger in the syringe barrel while providing tactile feedback of dose progression of the injectable material.

The plunger rod can include a thumb press located at a proximal end of the plunger rod such that application of the distally directed force to the plunger rod results in disengagement and reengagement of the counter member with the sequentially spaced periodic features on the plunger rod. The periodic features can comprise angled teeth and the angled surface of the teeth act to push the counter member out of the way so that the plunger rod can advance within the syringe barrel. The device can also include an actuating member having at least one tab having an engagement end and a finger press end and wherein application of a pivoting force to the at least one tab results in disengagement and reengagement of the counter member with the sequentially spaced periodic features on the plunger rod enabling retraction of the plunger rod and plunger within the syringe barrel.

The periodic features can be provided on oppositely disposed sides of the plunger rod and the counter member can comprise a pair of oppositely disposed tabs, each of the tabs including an engagement end and a finger press end and wherein the engagement end engages the periodic features. The oppositely disposed tabs can be configured to pivot upon the application of a squeezing force to the finger press ends of the tabs, causing the engagement end of the tabs to disengage from the periodic features, enabling retraction or advancement of the plunger rod and plunger in the syringe barrel.

According to one embodiment, the counter member can comprise a collar configured for clamping about a distal end of the syringe barrel. The collar of the counter member can comprise a plurality of separable components and the method of retrofitting the syringe includes permanently securing the separable components about a flange of the syringe barrel, such that the collar of the counter member overhangs a rear opening of the syringe barrel.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DESCRIPTION OF THE INVENTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is now made to FIGS. 1A-1B, 2A-2C, and 3A-3E, which show a controlled delivery syringe device, generally indicated as 10, in accordance with an embodiment of the present invention. The controlled delivery syringe device 10 includes a syringe barrel 12 having a proximal end 14 and a distal end 16. The syringe barrel defines a chamber 20 configured for containing an injectable material. The distal end 16 can include an opening, such as a luer lock opening 18, through which the injectable material can be expelled and a protective cap 19. It can be appreciated that other types of attachment arrangements can be provided for securing the distal end 16 of the syringe barrel 12 for expelling the injectable material into a target location.

Figure 4:
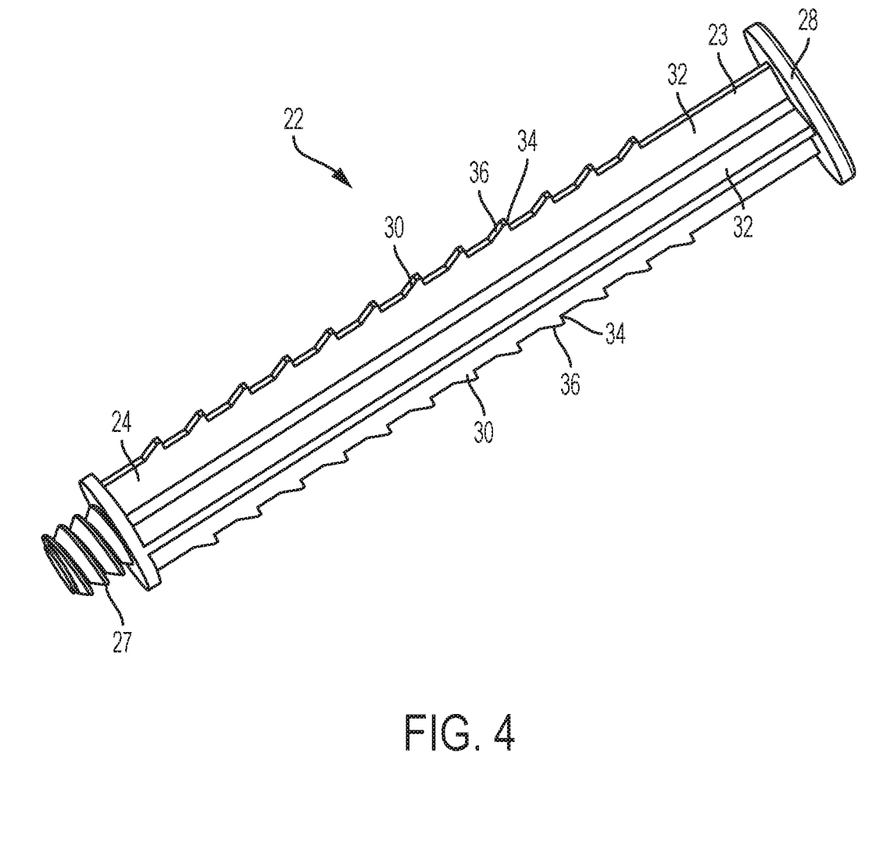
FIG. 4 is a side perspective view of the plunger rod used in the controlled delivery syringe device in accordance with an embodiment of the invention.

With continuing reference to FIGS. 1A-1B and 2A-2C and further with reference to FIG. 4, a plunger rod 22 is associated with the syringe barrel 12. The plunger rod 22 includes a proximal end 23 and a distal end 24. A plunger or stopper 26 is associated with or secured to the distal end 24 of the plunger rod 22. According to one embodiment, the plunger rod 22 can be threadedly secured to the plunger 26, as shown by 27 in FIG. 2B. It can be appreciated that the plunger rod 22 and plunger 26 can be secured by other techniques known in the art.

The plunger 26 is axially movable within the syringe barrel 12 to expel fluid from the opening 18 of the syringe barrel 12. The plunger rod 22 can also include a thumb press 28 located at the proximal end 23 of the plunger rod 22. A plurality of equally spaced periodic features 30, such as teeth, are provided on at least a portion of the plunger rod 22. The periodic features or teeth 30 can be located on one side of the plunger rod 22 or alternatively a set of teeth can be located on opposite sides of the plunger rod 22. According to one design, the periodic features or teeth 30 can be notched out of oppositely disposed splines 32 of the plunger rod 22.

Figure 1A:
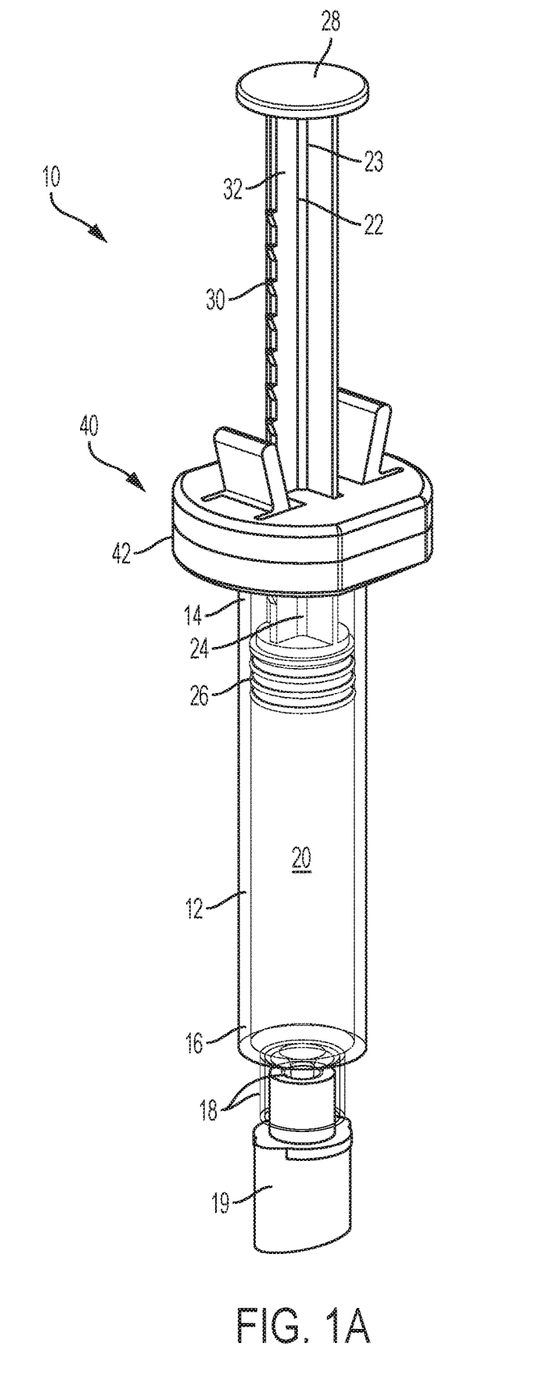
FIG. 1A is a right perspective view of the controlled delivery syringe device in accordance with an embodiment of the present invention.
Figure 1B:
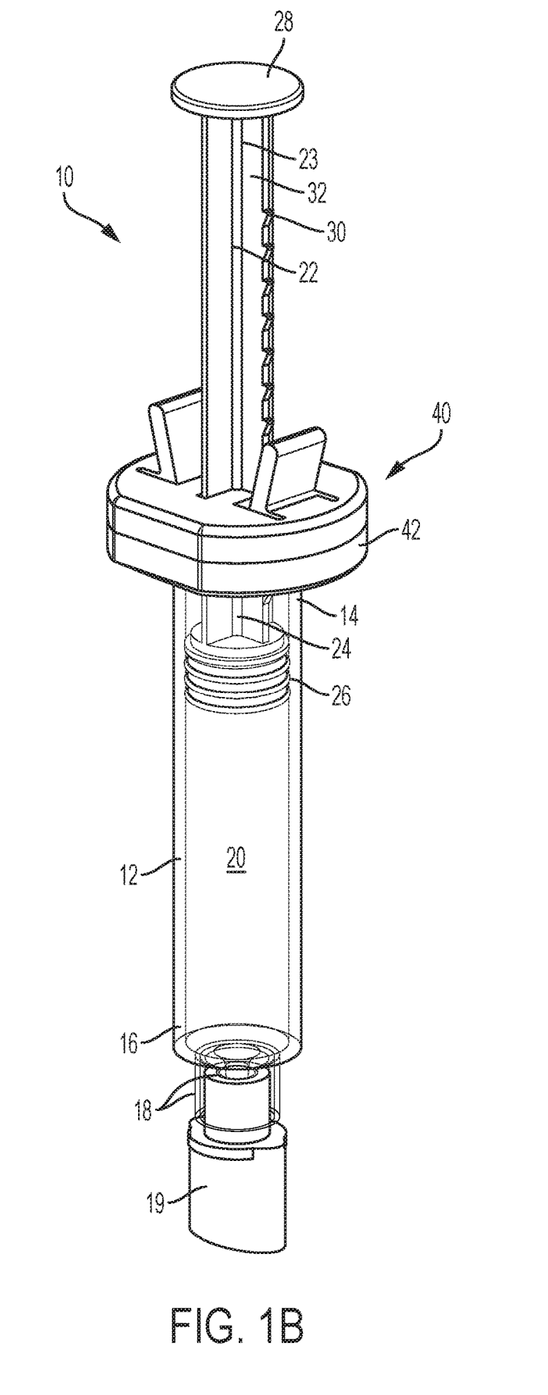
FIG. 1B is a left perspective view of the controlled delivery syringe device in accordance with an embodiment of the present invention.
Figure 2A:
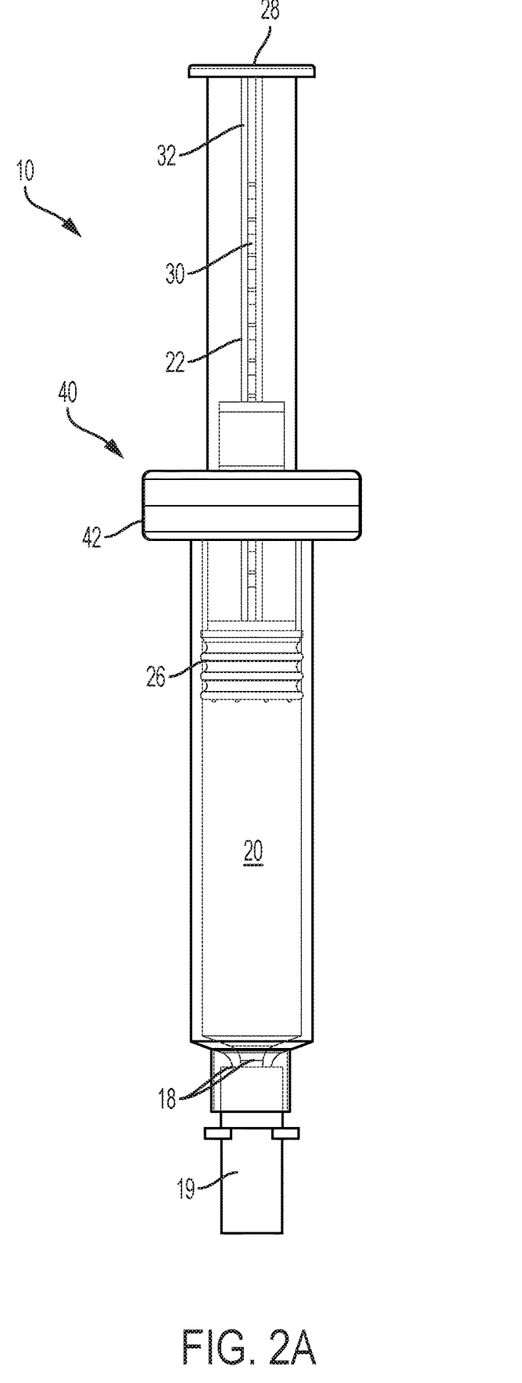
FIG. 2A is a front view of the controlled delivery syringe device of FIG. 1A in accordance with an embodiment of the present invention.
Figure 2B:
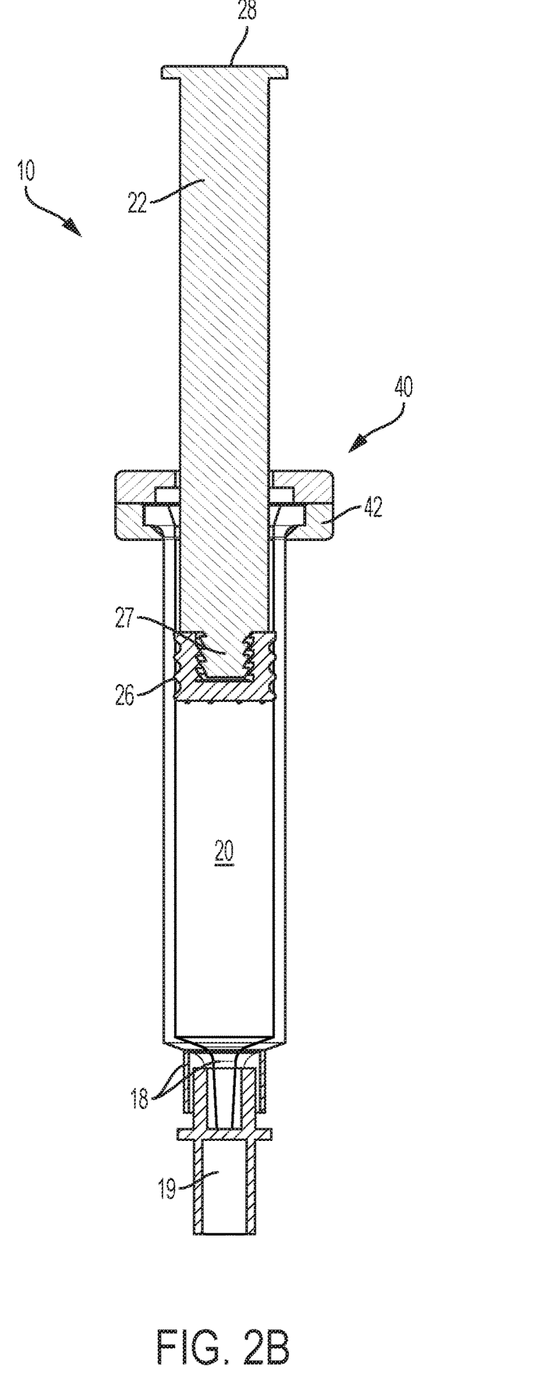
FIG. 2B is a cross-sectional view of the controlled delivery syringe device of FIG. 2A in accordance with an embodiment of the present invention.
Figure 2C:
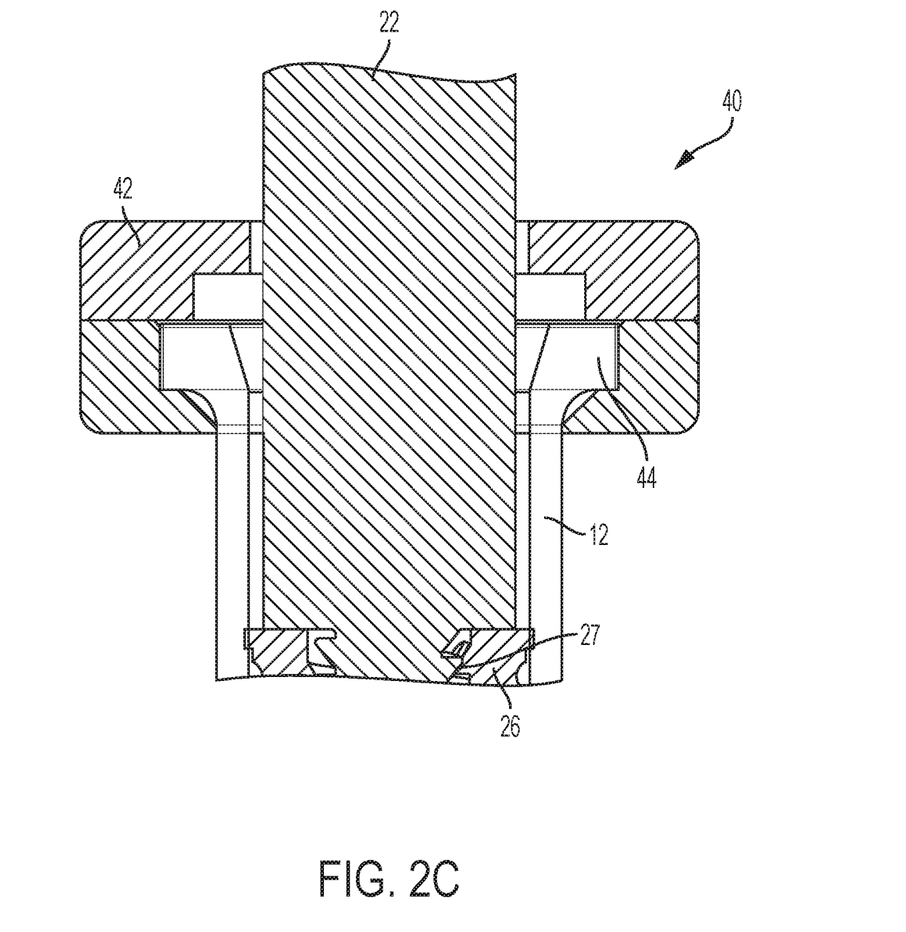
FIG. 2C is an enlarged view of a counter member of the controlled delivery syringe device of FIG. 2B in accordance with an embodiment of the present invention.
Figure 3A:
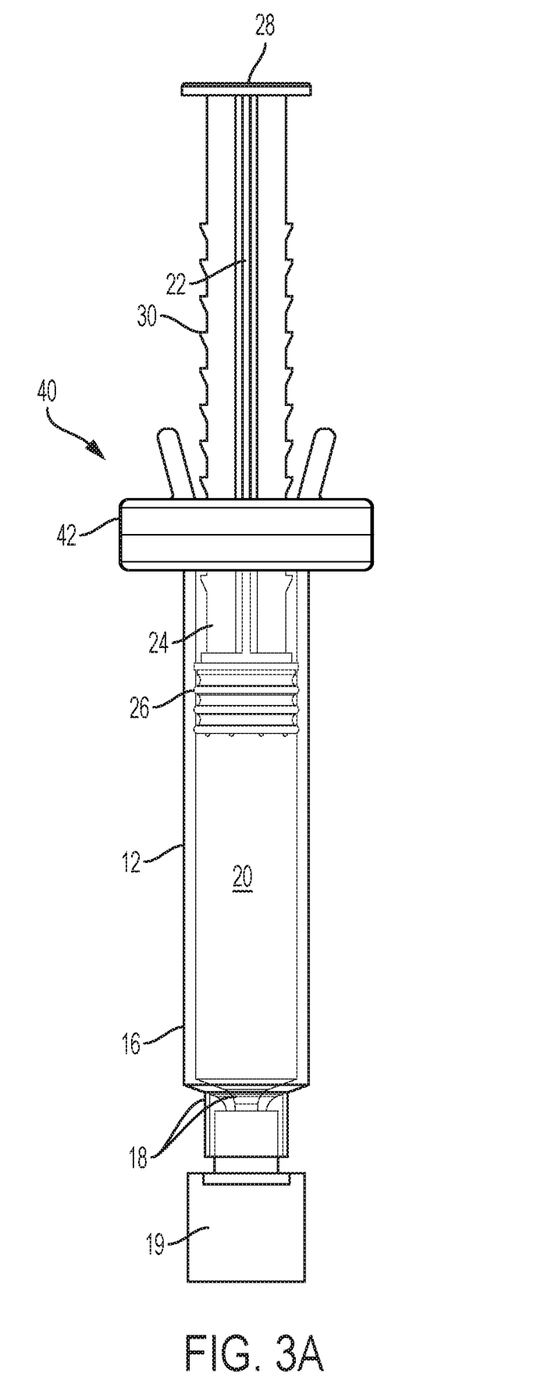
FIG. 3A is a right side view of the controlled delivery syringe device of FIG. 1A in accordance with an embodiment of the present invention.
Figure 3B:
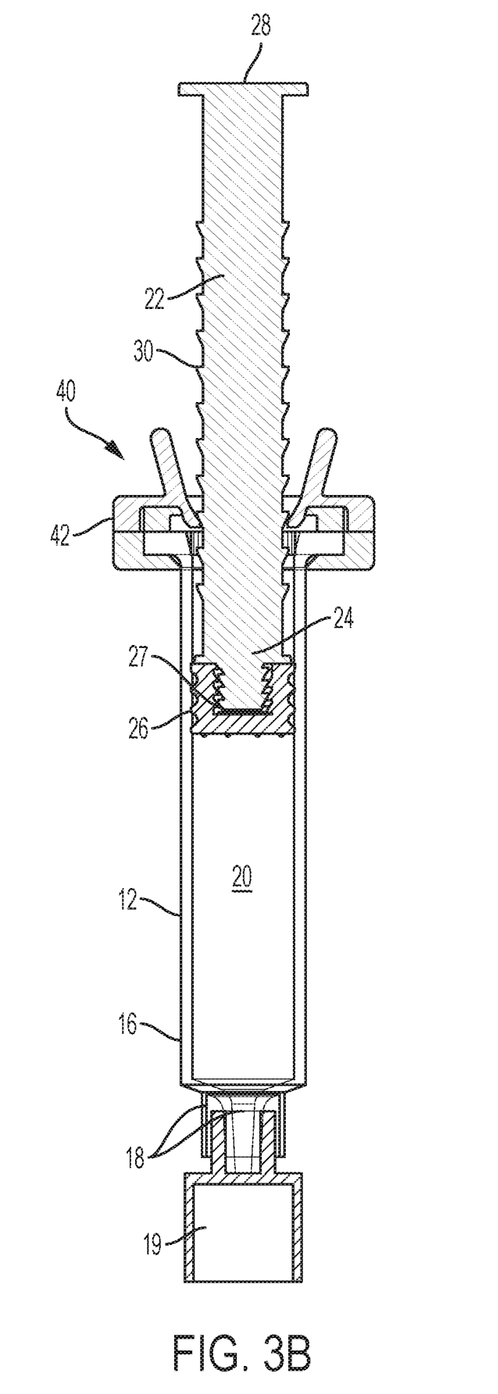
FIG. 3B is a cross-sectional view of the controlled delivery syringe device of FIG. 3A in accordance with an embodiment of the present invention.
Figure 3C:
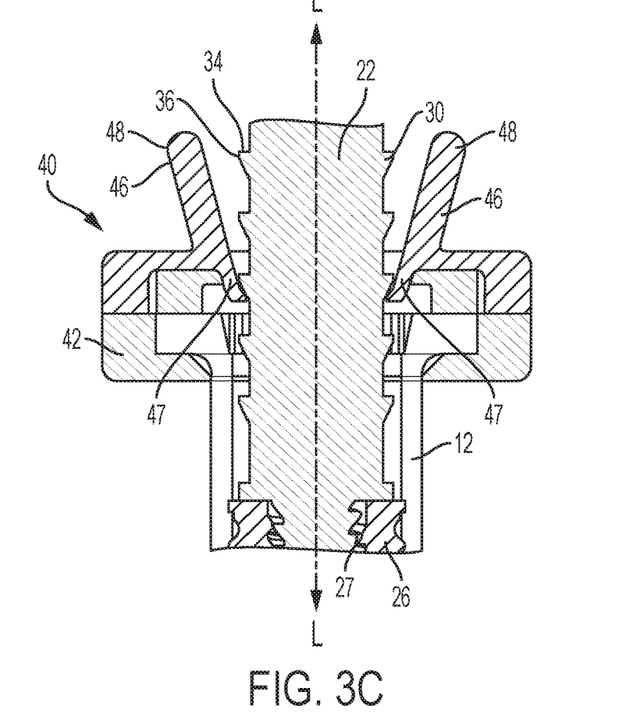
FIG. 3C is an enlarged view of a counter member of the controlled delivery syringe device of FIG. 3B in an initial state in accordance with an embodiment of the present invention.
Figure 5A:
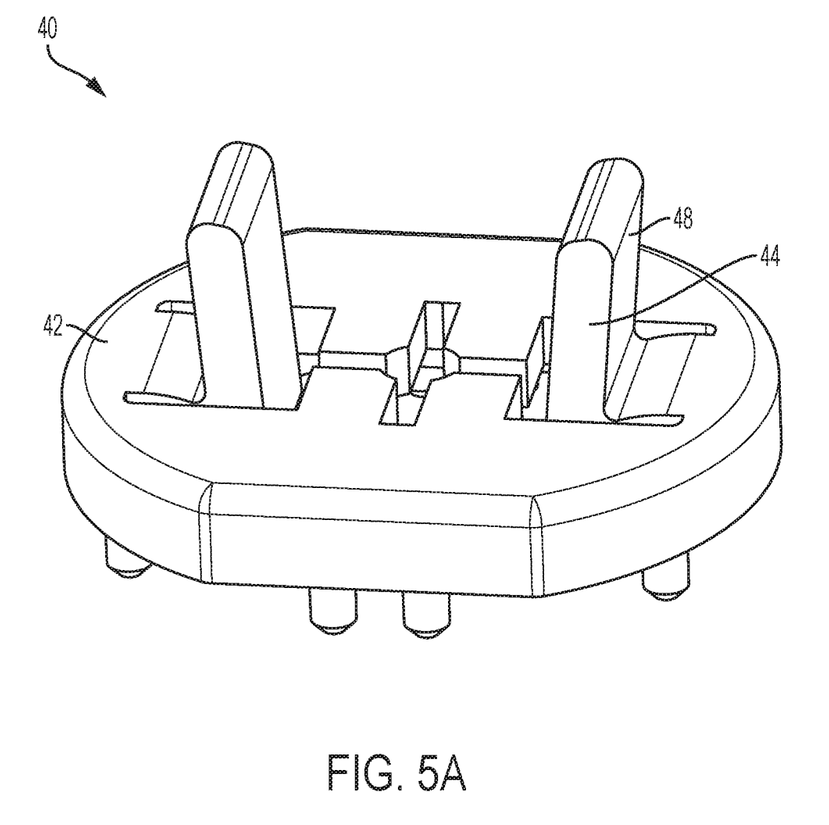
FIG. 5A is a top perspective view of the counter member used in the controlled delivery syringe device in accordance with an embodiment of the invention.
Figure 5B:
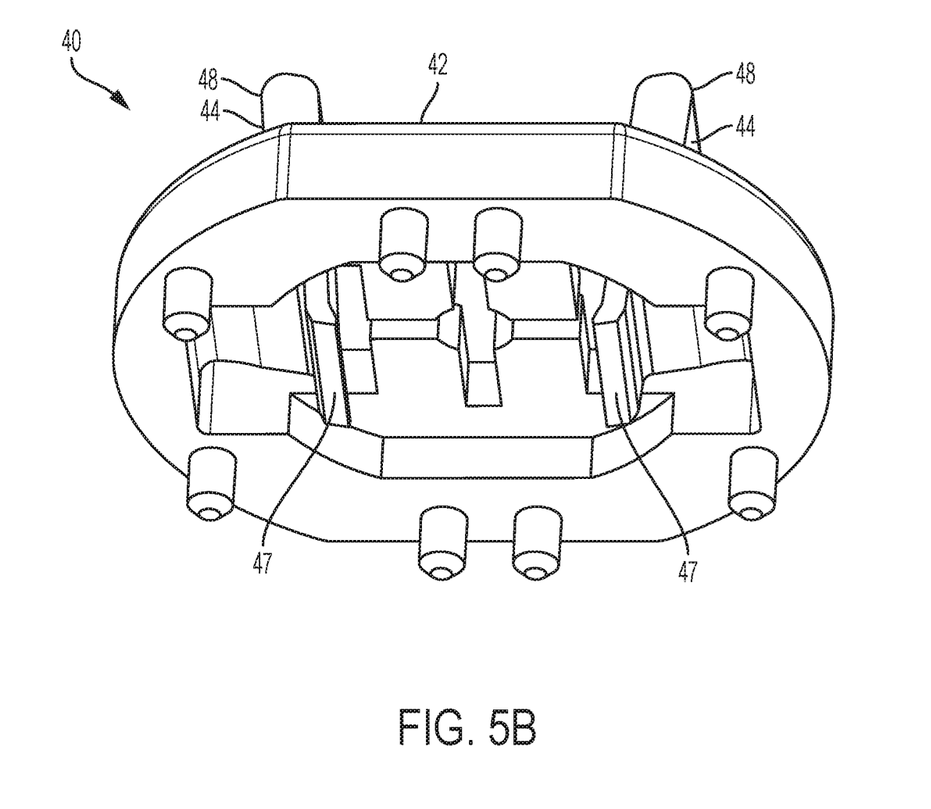
FIG. 5B is a bottom perspective view of the counter member used in the controlled delivery syringe device in accordance with an embodiment of the invention.

With continuing reference to FIGS. 3A-3E and further with reference to FIGS. 5A-5B, a counter member, generally indicated as 40, is engageable with the periodic features or teeth 30. With particular reference to FIGS. 3C and 4, the periodic features or teeth 30 can be shaped and oriented to cooperate with the counter member 40 during advancement of the plunger in the syringe barrel 12 to produce a sudden change in the actuation force, thus, generating a tactile signal upon application of a metered dose. In particular, the periodic feature or teeth 30 can include a flat surface 34 located behind each of the teeth 30 and a tapered or angled portion 36 that extends from the flat surface 34 and tapers downwardly in an inward direction with respect to a longitudinal axis L extending through the plunger rod 22. The counter member 40 includes a collar 42 that can be retrofitted and/or permanently attached to the proximal end 14 of the syringe barrel 12. This collar 42 can overhang the rear opening of the syringe barrel 12. As shown in the figures, the collar 42 can be formed of a plurality of interconnecting pieces that can be clamped about the rear collar 44 of the syringe barrel 12.

Figure 3D:
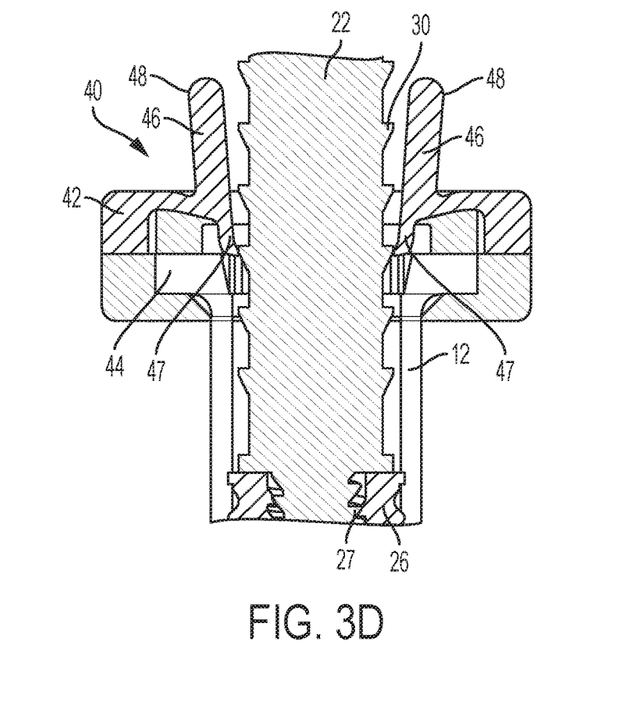
FIG. 3D is an enlarged view of a counter member of the controlled delivery syringe device of FIG. 3B in a deflected state in accordance with an embodiment of the present invention.
Figure 3E:
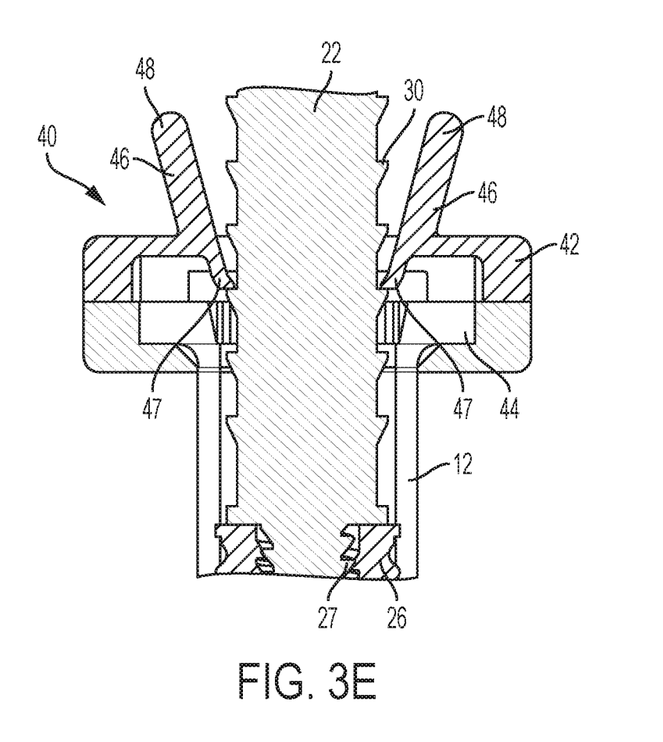
FIG. 3E is an enlarged view of a counter member of the controlled delivery syringe device of FIG. 3B in a returned state in accordance with an embodiment of the present invention.

With continuing reference to FIGS. 3A-3E and FIGS. 5A-5B, the counter member 40 can include either one or a pair of tabs 46 that include an engagement end 47 that interacts or engages with the periodic features or teeth 30. During use of the device, application of the distally direct force to the plunger rod 22 results in disengagement and reengagement of the engagement end 47 of the tabs 46 with sequentially arranged periodic features or teeth 30 on the plunger rod 22. In particular, as shown in FIGS. 3C-3E, upon actuation of the actuating member to inject a dose of the injectable material, the engagement ends 47 of the tabs 46 are deflected from an initial state, as shown in FIG. 3C, in an outward direction with respect to the teeth 30 and the longitudinal axis L of the plunger rod 22, to a deflected state, as shown in FIG. 3D, wherein the engagement ends 47 of the tabs 46 slide along the tapered or angled surface 36 of the teeth 30 essentially pushing the engagement end 47 in an outward direction out of the way allowing the plunger rod 22 and plunger 26 to advance in the distal direction to administer a dose of injectable material, and finally to a returned state, as shown in FIG. 3E. Upon reaching the returned state, the engagement ends 47 of the tabs become reengaged with the teeth 30 to lock the plunger rod 22 and plunger 26 in place. This sudden change in actuation force is perceived by the medical practitioner, thus, providing tactile feedback of dose progression of the injectable material. The tabs 46 are configured such that they automatically lock onto the teeth 30 when in an unbiased or non-actuated state. According to one example, the tactile feedback occurring from the engagement end 47 of the tab 46 deflecting over the toothed plunger rod 22 was measured and it was found that for approximately every 5 mm of displacement, a noticeable increase and decrease in force of about 1 N was measured when the teeth 30 passed the engagement end 47 of the deflecting tab 46.

The plunger rod 22 can include the thumb press 28 located at the proximal end 23 of the plunger rod 22 for receiving the distally directed force applied by the medical practitioner resulting in the disengagement and reengagement of the tabs 46 of the counter member 40 with sequentially spaced periodic features or teeth 30 on the plunger rod 22.

An actuating member can be provided that includes the at least one tab 46, which is associated with the counter member 40. In particular, the at least one tab or tabs 46 can include finger press ends 48. In order to release the engagement ends 47 of the tabs 46 from the teeth 30, a squeezing force can be applied to the finger press ends 48 of the tab 46, causing the engagement ends 47 to pivot in an outward direction, resulting in disengagement and reengagement of the counter member with sequentially spaced periodic features or teeth 30 on the plunger rod 22. The actuating member enables the technician to retract the plunger during administration of the injectable material. The tabs 46 are configured such that they can be squeezed out of the way when desired, but automatically lock onto the plunger rod teeth 30 when they are not being squeezed.

In accordance with one embodiment, the geometry of the tab 46 is such that the deflection of the tab 46 when advancing the plunger rod 22 is maximized for a given actuation force. According to yet another embodiment, the geometry of the tab 46 can include a vertical reinforcing member (not shown), to stiffen the tab 46 to withstand pressure from a dialysis line.

An advantage of this invention is that it allows the medical practitioner to count the number of times a "click" is felt during the administration of the injectable material. Since the spacing between the "clicks" is equivalent to a prescribed volume, the practitioner will readily know how much volume has been injected without looking at the graduations on the syringe barrel 12. For example, if the spacing between two neighboring periodic features or teeth 30 on the plunger rod 22 correspond to a 0.2 ml volume, the practitioner will know that a volume of 1 ml has been delivered after counting five "clicks". Another advantage of the invention is that it prevents backward travel of the plunger rod 22 before exiting the barrel. For example, during administration into a dialysis extracorporeal blood line, if the syringe 10 is left unclamped or if the clamp fails, the plunger rod 22 cannot be inadvertently pushed back and out of the barrel. Thus, the risk of catastrophic blood spill events is greatly reduced.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of this description. For example, it is to be understood that the present invention contemplates that, to the extent possible, one or more features of any embodiment can be combined with one or more features of any other embodiment.

The invention claimed is:

1. A controlled delivery syringe device comprising:
    a syringe barrel having a proximal end and distal end and defining a chamber therein, the chamber configured for containing an injectable material;
    a plunger rod associated with the syringe barrel;
    a plunger secured to the plunger rod and axially movable within the syringe barrel;
    a plurality of equally and sequentially spaced periodic features associated with at least a portion of the plunger rod; and
    a counter member engageable with the periodic features, wherein application of a distally directed force to the plunger rod results in disengagement and reengagement of the counter member with the sequentially spaced periodic features on the plunger rod, enabling advancement of the plunger rod and plunger in the syringe barrel while providing tactile feedback of dose progression of the injectable material;
    wherein the counter member comprises a pair of oppositely disposed tabs, each of the tabs including an engagement end and a finger press end, and wherein the engagement end engages the periodic features; and
    wherein the oppositely disposed tabs pivot upon the application of a squeezing force to the finger press end of the tabs, causing the engagement end of the tabs to disengage from the periodic features, enabling retraction or advancement of the plunger rod and plunger in the syringe barrel.

2. The device of claim 1, wherein the plunger rod includes a thumb press located at a proximal end of the plunger rod to receive the application of the distally directed force to the plunger rod and wherein the periodic features are tapered to apply an outwardly directed force to the counter member resulting in disengagement and reengagement of the counter member with the sequentially spaced periodic feature on the plunger rod.

3. The device of claim 1, wherein the periodic features are provided on oppositely disposed sides of the plunger rod.

4. The device of claim 1, wherein the counter member comprises a collar configured for clamping about a distal end of the syringe barrel.

5. The device of claim 4, wherein the collar of the counter member comprises a plurality of separable components capable of being permanently secured about a flange of the syringe barrel, such that the collar of the counter member overhangs a rear opening of the syringe barrel.

6. The device of claim 1, wherein the periodic features are configured to prevent inadvertent removal of the plunger rod out of the syringe barrel.

7. A method of retrofitting a syringe with a device for injecting a metered dose of injectable material comprising:
    providing a syringe barrel having a proximal end and distal end defining a chamber therein, the chamber configured for containing an injectable material;
    providing a plunger rod having a proximal end and a distal end and a plunger secured to the distal end thereof, the plunger rod further including a plurality of equally and sequentially spaced periodic features located thereon;
    associating the plunger rod and plunger with the syringe barrel such that the plunger is axially movable within the syringe barrel; and
    securing a counter member onto a distal end of the syringe barrel, the counter member including a pair of oppositely disposed tabs, each of the tabs including an engagement end and a finger press end, wherein the engagement end engages the periodic features,
    wherein application of a distally directed force to the plunger rod results in disengagement and reengagement of the counter member with a sequentially spaced periodic feature on the plunger rod, enabling advancement of the plunger rod and plunger in the syringe barrel while providing tactile feedback of dose progression of the injectable material; and
    wherein the oppositely disposed tabs pivot upon the application of a squeezing force to the finger press end of the tabs, causing the engagement end of the tabs to disengage from the periodic features, enabling retraction or advancement of the plunger rod and plunger in the syringe barrel.

8. The method of claim 7, wherein the plunger rod includes a thumb press located at a proximal end of the plunger rod to receive application of the distally directed force to the plunger road and wherein the periodic features are tapered to apply an outwardly directed force to the counter member resulting in disengagement and reengagement of the counter member with the sequentially spaced periodic features on the plunger rod.

9. The method of claim 7, wherein the periodic features are provided on oppositely disposed sides of the plunger rod.

10. The method of claim 7, wherein the counter member comprises a collar configured for clamping about a distal end of the syringe barrel.

11. The method of claim 10, wherein the collar of the counter member comprises a plurality of separable components and wherein the method of retrofitting the syringe includes permanently securing the separable components about a flange of the syringe barrel, such that the collar of the counter member overhangs a rear opening of the syringe barrel.

12. A controlled delivery syringe device comprising:
- a syringe barrel having a proximal end and distal end and defining a chamber therein, the chamber configured for containing an injectable material;
- a plunger rod associated with the syringe barrel;
- a plunger secured to the plunger rod and axially movable within the syringe barrel;
- a plurality of equally and sequentially spaced periodic features associated with at least a portion of the plunger rod; and
- a counter member engageable with the periodic features, the counter member comprising at least one tab having an engagement end and a finger press end;
- wherein application of a distally directed force to the plunger rod results in disengagement and reengagement of the engagement end with the sequentially spaced periodic features on the plunger rod, enabling advancement of the plunger rod and plunger in the syringe barrel while providing tactile feedback of dose progression of the injectable material; and
- wherein application of a pressing force to the finger press end, in a direction generally orthogonal to movement of the plunger rod, results in disengagement of the engagement end with the sequentially spaced periodic features on the plunger rod, enabling retraction of the plunger rod and plunger within the syringe barrel.

\* \* \* \* \*

UNITED STATES PATENT AND TRADEMARK OFFICE
CERTIFICATE OF CORRECTION

PATENT NO. : 11,628,258 B2
APPLICATION NO. : 16/604396
DATED : April 18, 2023
INVENTOR(S) : Mircea Despa et al.

It is certified that error appears in the above-identified patent and that said Letters Patent is hereby corrected as shown below:

In the Claims

Column 8, Line 51, Claim 8, delete "road" and insert -- rod --

Signed and Sealed this
Twentieth Day of June, 2023

Katherine Kelly Vidal
*Director of the United States Patent and Trademark Office*